United States Patent [19]
Johnson et al.

[11] Patent Number: 5,358,491
[45] Date of Patent: Oct. 25, 1994

[54] CARTRIDGE-NEEDLE UNIT HAVING RETRACTABLE NEEDLE

[75] Inventors: Kevin M. Johnson, Rochester; Dennis J. O'Dea, Macedon, both of N.Y.

[73] Assignee: Sterling Winthrop Inc., New York, N.Y.

[21] Appl. No.: 120,257

[22] Filed: Sep. 13, 1993

[51] Int. Cl.5 .............................................. A61M 5/145
[52] U.S. Cl. ..................................... 604/232; 604/195
[58] Field of Search ............... 604/232, 195, 110, 187, 604/218, 220

[56] References Cited

U.S. PATENT DOCUMENTS

| | | |
|---|---|---|
| 4,507,117 | 3/1985 | Vining et al. |
| 4,808,169 | 2/1989 | Haber et al. ............... 604/232 X |
| 4,909,794 | 3/1990 | Haber et al. |
| 4,935,014 | 6/1990 | Haber |

FOREIGN PATENT DOCUMENTS

| | | | |
|---|---|---|---|
| 26325 | 6/1902 | France | 604/232 |
| 2272688 | 12/1975 | Switzerland | 604/232 |

Primary Examiner—John D. Yasko
Attorney, Agent, or Firm—William J. Davis

[57] ABSTRACT

This invention relates to a novel cartridge-needle unit having a retractable needle for use with disposable or reusable holders to form safety syringes. The cartridge-needle unit comprises a cartridge comprising a hollow body, a septum at the distal end of the body, means for retaining the septum, and a plunger, axially and reciprocally slidable through the interior of the body; a needle capable of being withdrawn within the cartridge; a hub comprising a sleeve adapted to be snapped on the distal end of the cartridge; means for retaining the needle within the hub during an injection; and means for releasing the needle from the hub after the injection comprising an element capable of passing through the septum. The retractable cartridge-needle unit exhibits improved reliability, reduces the tendency for body fluids and/or medication to remain in an unprotected area upon retraction of the needle and virtually eliminates the possibility that the needle can be released into the patient.

27 Claims, 7 Drawing Sheets

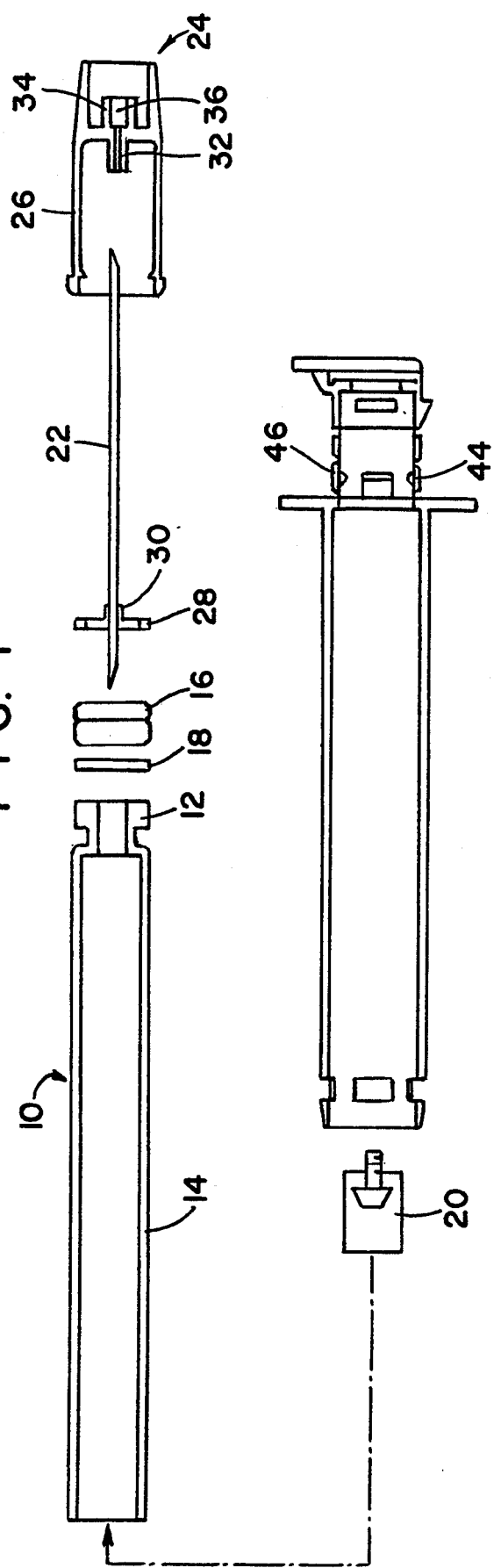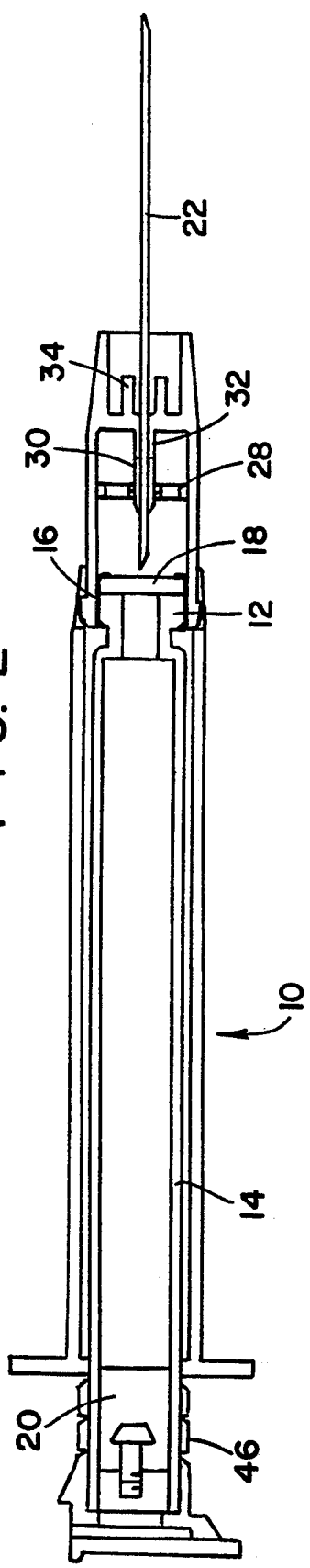

CARTRIDGE-NEEDLE UNIT HAVING RETRACTABLE NEEDLE

BACKGROUND OF THE INVENTION

1. Field of the Invention

This invention relates to a cartridge-needle unit having a needle that can retract within the cartridge after use for safe disposal and to a safety syringe comprising such cartridge-needle unit.

2. Description of the Prior Art

Disposable medicament-containing cartridge needle units for use in conjunction with reusable hypodermic syringe holders are well known in the art and in widespread commercial use. Such cartridges conventionally feature a cylindrical body closed at the proximal end with a flexible plunger slidable within the bore of the cartridge and closed at the distal necked-down end with a septum secured to the cartridge by a crimped-on aluminum collar. The necked-down distal end conventionally is fitted with a needle hub/needle/needle sheath assembly. Such cartridge-needle units are available from Sanofi Winthrop Pharmaceuticals under the Carpuject® trademark.

In use, the cartridge-needle unit must be activated, i.e., the proximal end of the needle cannula must penetrate the sealed septum such that communication is achieved between the fluid and the proximal end of the needle. Some cartridge-needle units are sold in an activated form. Others must be activated by the user. When user activated cartridge-needle units are used in conjunction with conventional reusable syringe holders of the type described, for example, in Hadtke, U.S. Pat. No. 4,585,445 and in EP-A 485,028, this is accomplished when the health care worker advances the cartridge through the holder by rotating a clamping element.

Many holders, including the above-referenced reusable holders, enable the user to avoid handling the cartridge-needle unit when the needle unit is exposed. Nevertheless, health care workers are especially susceptible to accidental and potentially infectious, and indeed, on occasion, possibly fatal, needle strikes due to the careless handling and/or disposing of the cartridge-needle unit after use. The consequences to health care workers of strikes from needles contaminated with various infectious diseases such as hepatitis or AIDS can be particularly severe. The frequency of accidental needle strikes in the United States is surprisingly great, and has been estimated to be approximately one million strikes per year. Moreover, the cost to health care organizations for the testing of health care workers accidentally stricken by used needles is a significant burden on health care costs. This is illustrated in a recent report by Kirkland, *Safer Syringes Boost Molder Opportunities*, Plastics World, August 1993, pp. 20-24, which states:

"The average cost associated with accidental needle-stick injury in the U.S. reportedly is $3 billion/year. For example, estimates for the average cost associated with testing alone is at least $1,200 per injury. This does not take into account the cost of treatment if disease develops (estimated at $15,700), litigation costs, increased insurance premium costs, replacement of the injured worker, OSHA fines and other costs."

Therefore, it would be desirable to further protect health care workers by providing systems which reduce the possibility of accidental needle strikes.

To this end, it has been suggested to provide syringes having a retractable needle. For example, Haber et al, U.S. Pat. No. 4,909,794, describe a combination retractable needle cannula and cannula lock for a medication carpule, i.e., cartridge. The cannula lock includes a clamp having a pair of jaws which are normally separated from one another so that the needle can be releasably retained therebetween. In the pre-injection state, the clamp is axially spaced from the cartridge, and the jaws of the clamp are rotated towards one another to retain the cannula in an axially extended position for administering an injection. Post-injection, the health care worker continues to apply pressure to the piston stem forcing the empty cartridge to move forward such that the needle embeds in the plunger. Further movement displaces the clamp, whereby the jaws of the clamp rotate away from one another to release the cannula. The cannula may then be retracted within and completely surrounded by the empty cartridge so that the cannula can be safely discarded.

However, the system proposed in U.S. Pat. No. 4,909,794 has been found to be less than satisfactory from a commercial standpoint for a variety of reasons, resulting from both inherent design limitations and reliability concerns.

First, because the needle is released from the jaws of the clamp by the health care worker continuing to apply an axially and distally directed force beyond the point at which all medication is delivered, there is an unacceptably high probability that the health care worker may prematurely release the needle while it is still embedded in the patient. One possible consequence of this may be that the health care worker must then remove a lone sharp needle from the patient.

Second, unlike most current commercial hypodermic syringe designs, this prior art system relies upon an interference fit between the jaws and the hub in order to wedge the needle in place. In fact, Haber et al suggest that the proximal surface of the cannula be textured to enhance the frictional retention of the needle. However, if the frictional force is not great enough, the needle may slip with respect to the jaw both upon injection and removal from the patient. If the fit is too tight and the frictional force is too high, the user may have to deliver an unreasonably high force to release the jaw from the hub. More generally, friction is an unreliable force to use for such a critical function, inasmuch as small variations in dimension, surface finish, cleanliness, or even temperature can alter the desired retention force. While some modifications can be made to improve the reliability of this device and its use of friction, ultimately, there are limitations.

Third, after the jaw is released from the hub, the needle is freed to be withdrawn into the cartridge by the plunger. However, any body fluid and/or medication that may remain on the tip of the needle after removal from the patient can be wiped on the jaw as the needle is retracted. This body fluid then remains in an unprotected area and presents some level of danger to the health care worker.

Haber, U.S. Pat. No. 4,935,014, which is a continuation-in-part of the above-described Haber et al patent, describes another combination retractable needle cannula and cannula lock embodiment in which the jaws of the clamp in the pre-injection state are surrounded by and rotated towards one another by an expandable outer sleeve which retains the cannula in an axially extended position between the jaws for administering an injection. Post-injection, the clamp is displaced outwardly of the sleeve, whereby the jaws are free to release the cannula. It appears that the sleeve enables the syringe to be adapted for use with a cartridge having a head which is narrower in diameter than the cylindrical body. In any event, the syringe described by Haber in U.S. Pat. No. 4,935,014 contains jaws and suffers from the same inherent design limitations and reliability concerns as described above.

It would be desirable to provide a cartridge-needle unit having a retractable needle which (1) reduces the tendency for body fluids and/or medication to remain in an unprotected area upon retraction of the needle into the cartridge, (2) does not rely upon an unpredictable frictional fit between the needle and hub and (3) virtually eliminates the possibility that the needle can be released into the patient.

SUMMARY OF INVENTION

We have discovered an improved cartridge-needle unit having a needle which can be retracted within the cartridge. The cartridge-needle unit does not rely upon a frictional fit to hold the needle in place and reduces the tendency for body fluids to remain in an unprotected area upon retraction of the needle into the cartridge, and virtually eliminates the possibility that the needle can be released into the patient.

More specifically, in accordance with this invention, there is provided a cartridge-needle unit comprising a cartridge comprising a hollow body, a septum at the distal end of the body, means for retaining the septum, and a plunger axially and reciprocally slidable through the interior of the body; a needle capable of being retracted within the cartridge, a hub comprising a sleeve adapted to be snapped on the distal end of the cartridge; means for retaining the needle within the hub during an injection; and means for releasing the needle from the hub after the injection comprising an element attached to the needle which is capable of passing through the septum.

It is an advantageous feature of this invention that a cartridge-needle unit having a retractable needle is provided that virtually eliminates the possibility that the needle can be released into the patient.

It is another advantageous feature of this invention that a cartridge-needle unit having a retractable needle is provided having substantially improved reliability, thus reducing the susceptibility of health care workers to accidental needle strikes.

Another advantageous feature of this invention is that a retractable needle cartridge-needle unit is provided that reduces the tendency for body fluids and/or medication to remain in an unprotected area upon retraction of the needle into the cartridge.

Still another advantageous feature of this invention is that a retractable needle cartridge-needle unit is provided which can be used in conjunction with conventional commercially available prefilled medication cartridges and both disposable and reusable holders.

Other advantages will become readily apparent upon reference to the following description of preferred embodiments when read in light of the accompanying drawings.

BRIEF DESCRIPTION OF THE DRAWINGS

FIG. 1 is a cross-sectional exploded view of a preferred embodiment of a cartridge-needle unit of this invention and an associated disposable holder.

FIG. 2 is a cross-sectional view of the embodiment of FIG. 1 in an assembled position.

DESCRIPTION OF PREFERRED EMBODIMENTS

Figure 3:
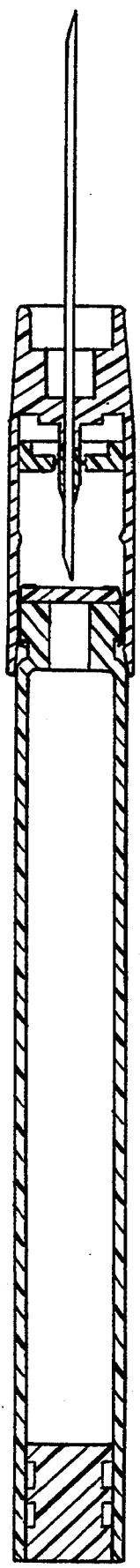
FIGS. 3-7 are cross-sectional views of a cartridge needle in accordance with this invention illustrating the sequence of operation.
Figure 4:
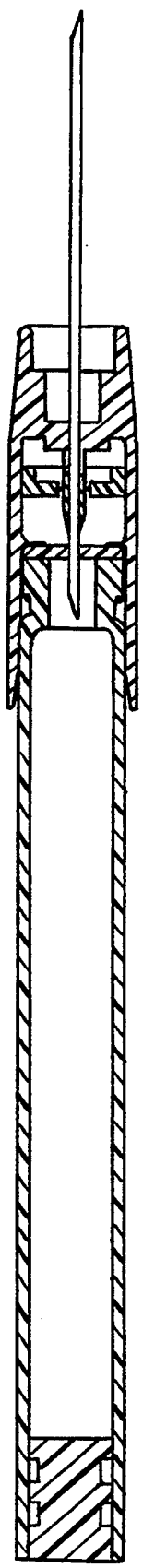
Figure 5:
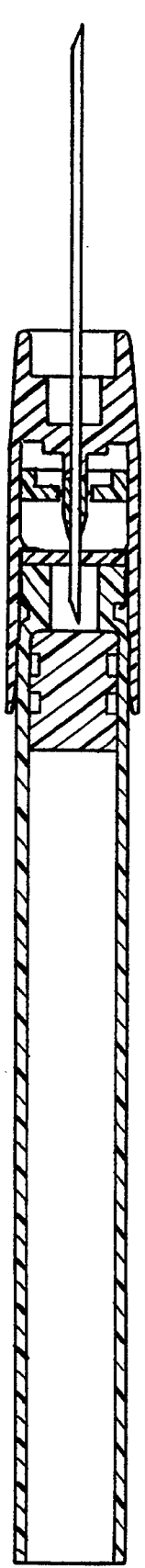
Figure 6:
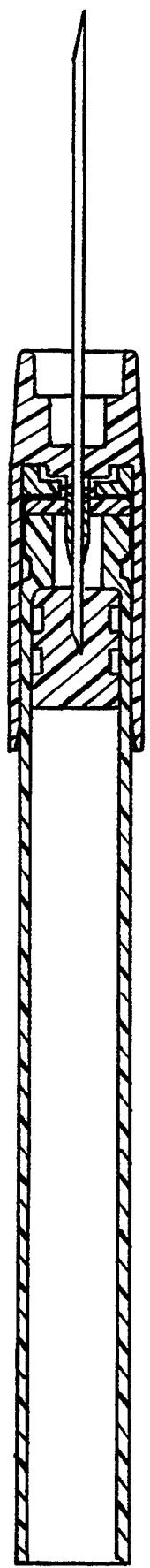
Figure 7:
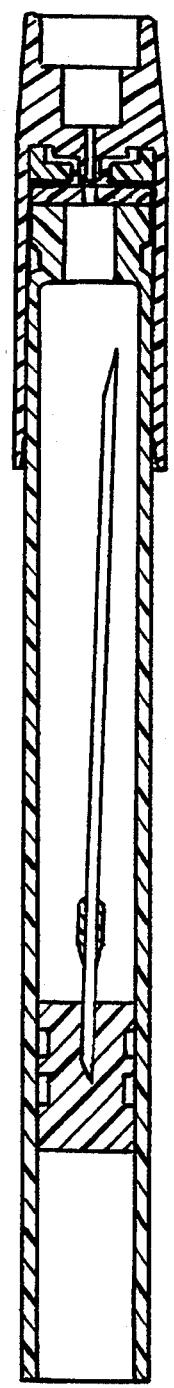
Figure 8:
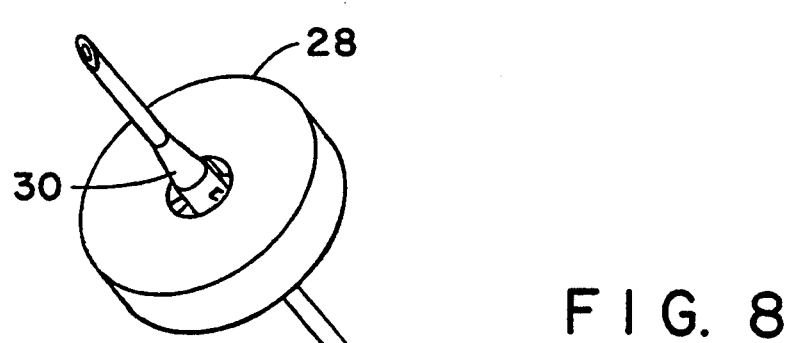
FIGS. 8 and 9 are perspective views of a washer-dart-needle combination in accordance with a preferred embodiment of this invention.
Figure 9:
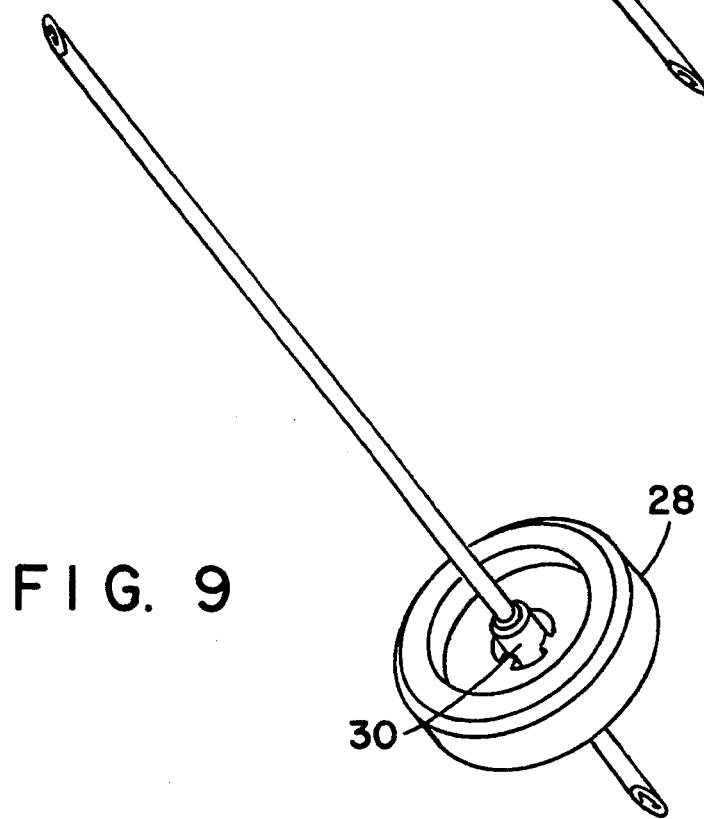
Figure 10:
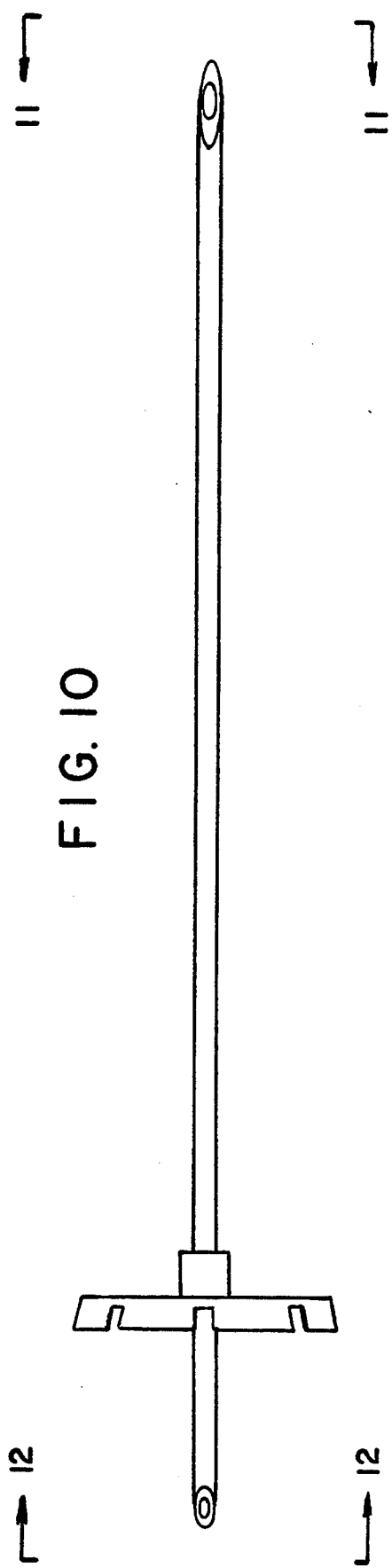
FIGS. 10-12 are side, distal and proximal views of another washer-dart-needle combination in accordance with this invention.
Figure 12:
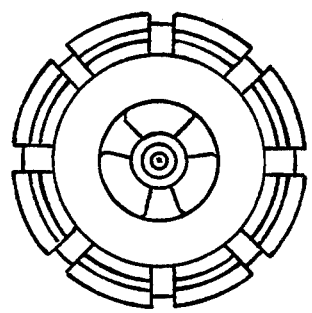
Figure 11:
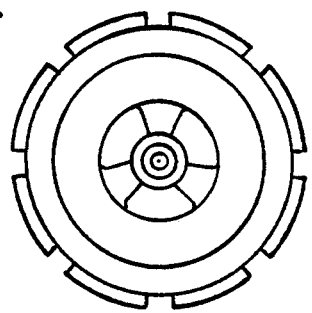

This invention is hereinafter described particularly in regard to preferred embodiments featuring a prefilled medication cartridge which is activated by the health care worker and a safety syringe assembly. In addition, this invention is useful in conjunction with a wide variety of syringe assemblies featuring both disposable and reusable holders including those designed for use with cartridge-needle units that are sold in an activated form, and with other devices adapted to dispense fluids.

In a preferred embodiment, the cartridge-needle unit of this invention is used in conjunction with an activatable prefilled cartridge, preferably containing a fluid medication or the like. Illustrated in FIG. 1, prefilled cartridge 10 can be of a conventional design and can include a hollow transparent body, typically fabricated of glass. The cartridge can include head portion 12 and cylindrical body 14 which are coextensively joined together at a relatively narrow neck.

The cartridge-needle unit comprises septum 18 at the distal end of the body. The septum prevents contamination and leakage of the fluid contents of the cartridge and forms an air-tight, sterile seal. The septum can be fabricated of compliant, resilient, rubbery materials which tend to reseal after being pierced. Preferred materials exhibit a Shore A durometer hardness of from about 50 to about 70. Septums fabricated of materials meeting these criteria are commercially available.

The cartridge-needle unit comprises means for retaining the septum. In a preferred embodiment, the means for retaining the septum can take the form of end cap 16 which covers the septum. The cap preferably is of a diameter approximately equal to that of the distal end of the glass cartridge. The cap holds the septum in place at the distal end of the cartridge. The cap can be fabricated of any suitable material, such as a metal such as aluminum. Alternatively, the septum can be adhered to the distal end of the cartridge using a suitable adhesive. In another embodiment, the septum can be retained within a slot or other retaining means disposed preferably at the mouth or neck portion of the cartridge.

The cartridge-needle unit comprises plunger 20 is sized to be received in and slidable axially and reciprocally through the interior of the cartridge. The plunger can be moved axially and distally through the cartridge for expulsing contents of the cartridge via needle cannula 22. The screw-threaded post extending proximally from the plunger can be mated to screw-threadable plunger rod of an associated holder for controlling the movement of the plunger through the interior of the cartridge. It is contemplated that the plunger rod can be attached to the plunger by various techniques. For example, the plunger rod can be attached directly to the plunger rod through a snap fit. Prefilled cartridges such as described above are currently in widespread commercial use. It is a particular advantage that this invention is useful in conjunction with cartridges in widespread commercial use.

In accordance with this invention, a cartridge-needle unit is provided with a needle hub/needle assembly as described below, and a needle sheath. Needle hub 24 comprises sleeve 26 which is designed to be snapped over the distal end of the cartridge, thus attaching the needle hub to the cartridge in a manner such that the cartridge can be forced forward in the hub after medication delivery. When an end cap is present, the hub sleeve can move over the sides of the cap. The hub, in conjunction with the needle sheath, forms a sterile seal for the enclosed septum and needle. The cartridge-needle unit comprises means for retaining the needle within the hub during an injection. The cartridge-needle unit further comprises means for releasing the needle from the hub after the injection. Such means comprises an element attached to the needle which is capable of passing through the septum.

In a preferred embodiment, the means for releasing the needle from the hub comprises a washer 28 and dart 30 attached to the needle. The dart in conjunction with hub post 32 or the like prevents movement of the needle forward with respect to the hub, virtually eliminating the possibility that the needle can be released into the patient. Additionally, the dart is capable of passing through the septum. The dart can be frangibly connected to the washer. The washer and dart preferably can be fabricated as a unitary piece by conventional injection molding techniques. The dart can be fabricated of a brightly colored plastic, which serves as an indicator that the needle has been safely withdrawn into the cartridge. After the medication has been delivered and the syringe removed from the patient, continued pressure on the plunger rod forces the cartridge forward, separating the dart from the washer. When this occurs, the dart is forced through the septum by means of the hub post and the needle becomes embedded in the plunger. The plunger rod can then be withdrawn, pulling the needle and dart completely within the cartridge. The proximal end of the dart preferably comprises a conical taper to facilitate passage through the septum. It is contemplated that the dart geometry and shape can vary depending, e.g., on the type of material to be penetrated. For example, the dart can be provided with a lengthy tapered body, and/or with one or more knife-like fins to facilitate penetration through the septum.

The dart preferably comprises an annular circumferential shoulder on the distal end which communicates with the proximal portion of the hub post, virtually eliminating the possibility that the needle can move forward with respect to the hub. As noted, this is a particular advantage of this invention inasmuch as prior art designs are susceptible to release of the needle into the patient.

A conventional needle, preferably a double ended needle, can be permanently affixed to the dart using conventional techniques, e.g., using conventional adhesives such as an epoxy.

Figure 15:
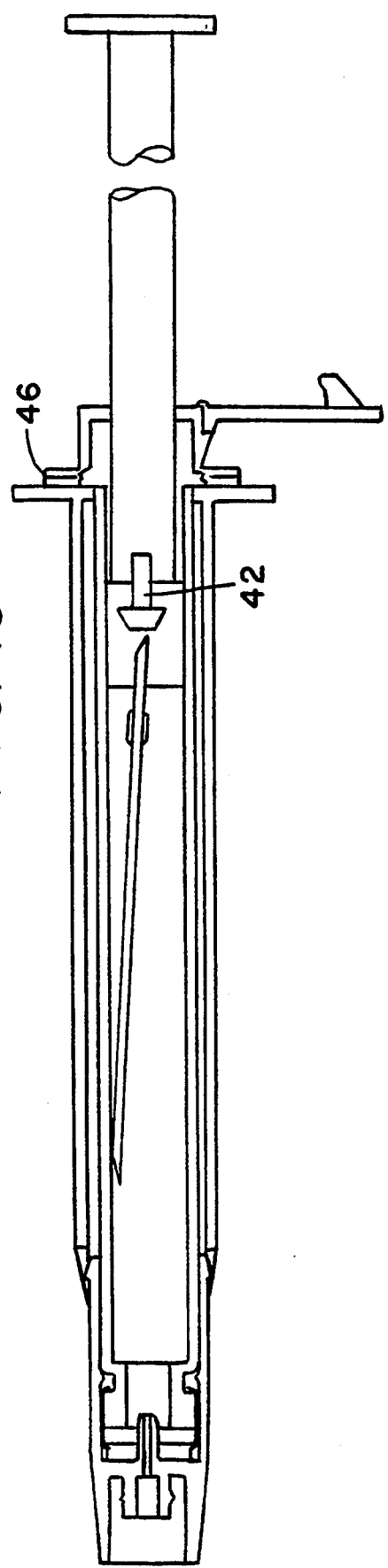
FIG. 15 is a cross section of a preferred embodiment of this invention after retraction wherein the plunger comprises a stud and the hub post protrudes through the septum.

The hub, which preferably is of a diameter approximately the same as the dart, forces the dart through the septum when continued pressure on the plunger rod after medication delivery thrusts the cartridge forward with respect to the hub. Additionally, the hub post helps orient the needle during assembly and use, and helps prevent the dart from exiting the syringe when it is forced at least partially through the septum as illustrated in FIG. 15. The hub can further comprise sheath post 34 having a cylindrical cavity therein, the diameter of which is slightly greater than the diameter of the needle such that recessed fluid well 36 is formed. The fluid well functions to retain any residual body fluid or medication left on the needle after it is withdrawn from the patient. The inner walls of the well can be provided with a slightly rougher surface finish to make them more receptive to wetting. The wall helps keep residual fluid out of both contact and sight. As noted, the fluid well provides an important safety advantage over the prior art. The outside diameter of the sheath post can be sized to accept the needle sheath and can comprise an annular circumferential seal ring to provide a sterile seal. The inside diameter of the hub preferably contains an annular ring or bumps to retain the washer and dart in the hub before and/or during injection.

Figure 13:
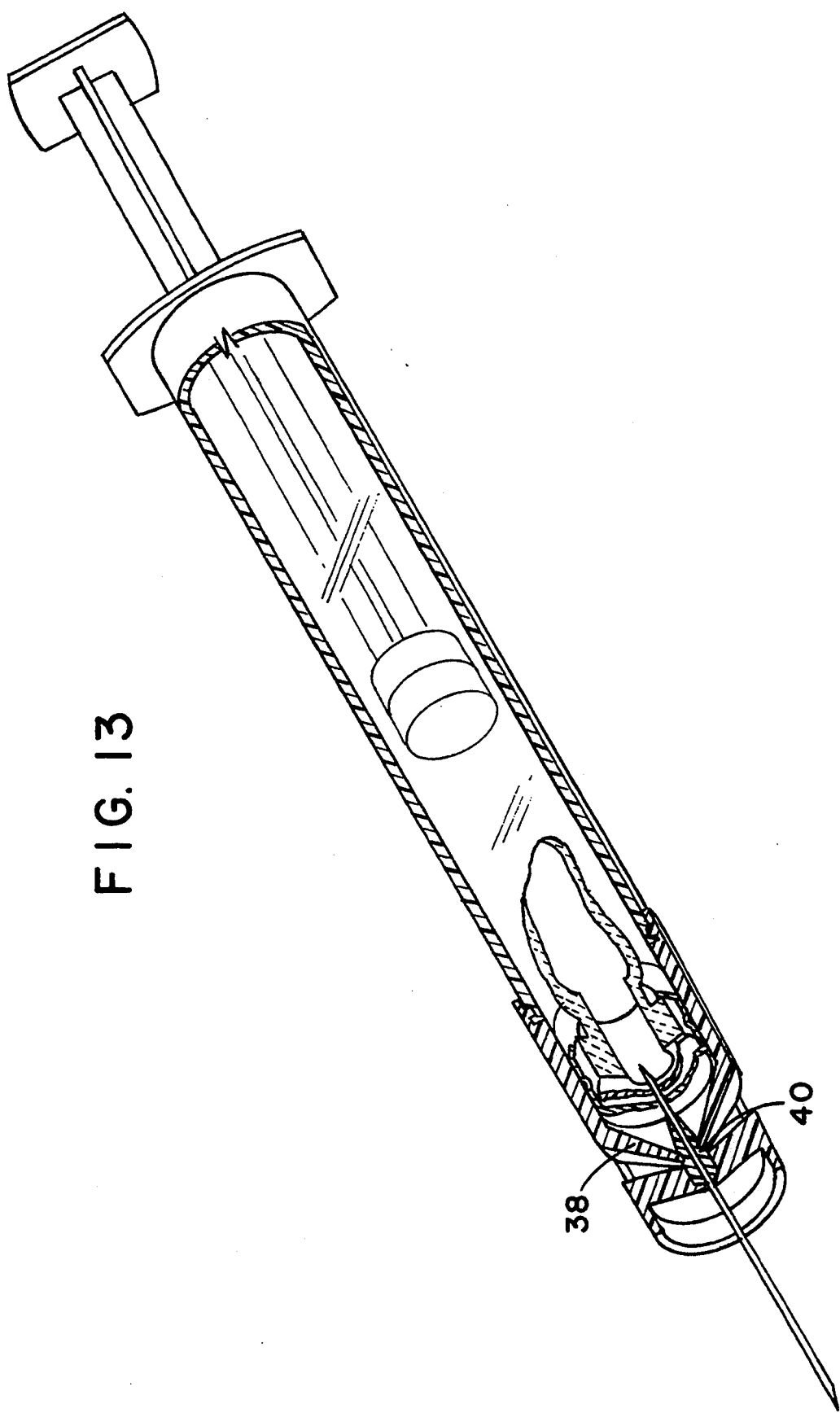
FIG. 13 is a perspective view of an alternative embodiment of this invention which features a dart retained in the hub by fingers.
Figure 14:
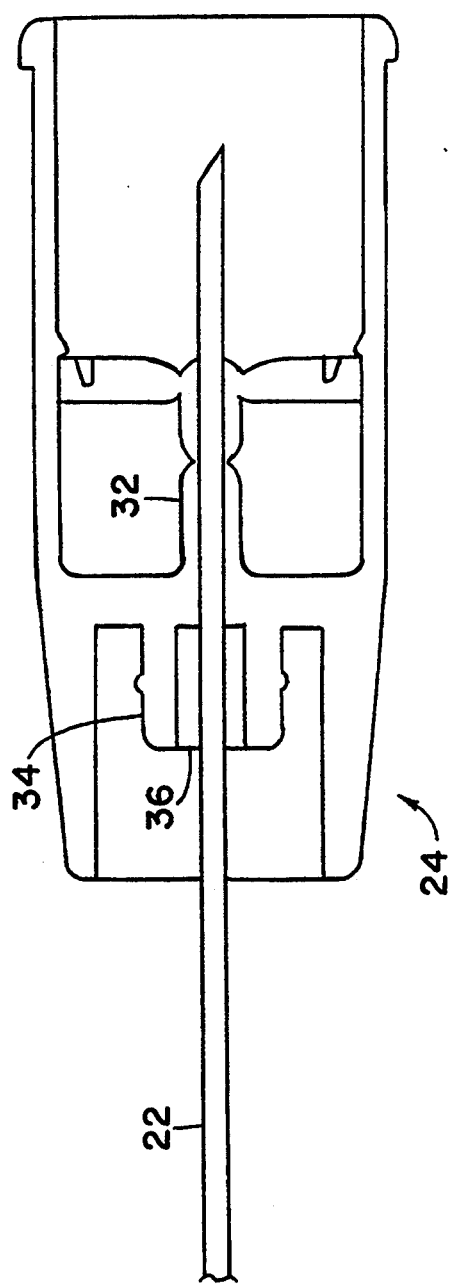
FIG. 14 is an enlarged cross-section of the hub-needle illustrated in FIG. 2.

In an alternative embodiment, the means for retaining the needle within the hub during the injection can comprise inwardly extending fingers 38, as depicted in FIG. 13, which hold the element, e.g., dart, attached to the needle by engaging slots 40 in the side of the dart. In this embodiment, the element attached to the needle need not be frangibly connected to the hub. Nevertheless, in use, after medication has been delivered and the syringe removed from the patient, continued pressure on the plunger rod forces the cartridge forward, separating the dart from the fingers, forcing the dart through the septum, and imbedding the needle into the plunger.

The cartridge-needle unit can be provided with means for tilting, i.e., offsetting the needle comprising a relatively resilient, non-compliant member. The non-compliant member can be fabricated of a rigid material, such as, for example, a metal or plastic. Compared to a compliant member, e.g., a rubber plunger, the non-compliant member can enhance the degree to which the needle is tilted or offset. In one embodiment, the plunger can be provided with an internal metal or rigid plastic plate. In another embodiment, the plunger rod can function as the means for tilting the needle, e.g., when the rod is attached directly to the plunger via a snap fit. In a preferred embodiment, the non-compliant member, upon contact with the needle, can cause the needle to deform, e.g., by bending the tip or body. Such deformation of the tip is advantageous inasmuch as it increases the force through which the needle is retained, e.g., in the plunger, thus facilitating reliable needle retraction. Additionally, the interference caused by the non-compliant member forces the needle to tilt or offset toward the cartridge well. When the retracted needle is tilted toward the cartridge wall and the cartridge-needle unit is provided with a hub post designed to protrude through the septum after retraction as described below, the retracted needle is virtually precluded from exiting the cartridge through the port in the hub, even in the event that the plunger is pushed axially and distally forward.

In a preferred embodiment, the plunger can comprise stud 42, FIG. 15, and the cartridge-needle unit and hub can be sized such that the needle tip contacts the plunger stud during the process of imbedding the needle in the plunger. This increases the propensity for the needle to tilt and increases the grabbing force by bending the fragile needle tip upon hitting the stud. The bent needle tip advantageously increases the force required to remove the needle from the plunger after it is imbedded therein. Moreover, the tilt makes it more difficult for the needle to be inadvertently forced out of the cartridge. In a preferred embodiment illustrated in FIG. 15, the hub post protrudes through the septum after retraction. This feature, in combination with the studded plunger, makes it virtually impossible for the needle to leave the cartridge after it has been withdrawn there within. Additionally, when the septum closes upon the hub post, i.e., when the dart goes fully through the septum, the septum advantageously provides no further resistance as the dart and needle are withdrawn into the cartridge. One distinct advantage of this invention is that it provides protection to the health care worker through removal of a sharp, used needle into the glass cartridge. This prevents the needle from puncturing gloves and/or skin and contaminating the health care worker with a potentially diseased body fluid of the patient. A less tangible but perhaps equally important aspect of the invention is the impression it makes upon the health care worker, i.e., by sealing the used needle safely within the glass, the user is convinced that the device is a safe one. As noted, by fabricating the dart of a brightly colored plastic, the dart functions as an indicator to the health care worker that the needle has been safely withdrawn within the cartridge. It is also contemplated that the needle can be brightly colored such that the needle functions as the indicator. For example, a portion of the needle can be provided with a coating of a brightly colored paint.

The hub, the means for retaining the needle in the hub and the means for releasing the needle from the hub can be fabricated of any suitable material including metals and plastic. However it is a particular advantage that the above-described designs are well adapted to be fabricated of plastic. In particular, it is preferred that the hub and means for retaining and releasing the needle be fabricated of rigid plastic using known precision injection molding techniques. Suitable plastics include, polypropylene, HIMONT plastics, polystyrene, polycarbonates, ABS (clear or opaque), nylon, acetals, such as DELRIN, polyethylene or polyester.

The cartridge-needle unit of this invention can be used in conjunction with any disposable or reusable holder appropriately sized to accept the cartridge-needle unit. In a preferred embodiment, the holder is disposable, i.e., a single use holder. A preferred holder, depicted in FIGS. 1 and 2, comprises a hollow body sized for housing the cartridge-needle unit therein. In a preferred embodiment, the holder is provided with a tamper evident "flip top" cap having a cam. The tamper evident cap allows the medical worker to remove the seal without having to dispose of a separate part. The cap remains out of the way during the sequence of medication delivery and safety activation.

In a particularly preferred embodiment, the holder is provided with an "over-travel" cap. Such cap prevents the contaminated needle and plunger from exiting the cartridge and creating a potential safety hazard. The over-travel cap can be molded integrally with the body, such that the process of activating the cartridge also locks the cap in place.

In a particularly preferred embodiment, the holder can be provided with a connecting member between the cap and the body of the holder. For example, the connecting member can be a relatively straight tether or set of tethers between the cap and body. The connecting member can comprise means for predisposing the connecting member to fold in a specified, e.g., outward, direction. For example, pairs of folding tethers 46 (FIGS. 1 and 15) permit the retaining over-travel cap and/or tamper evident flip top cap to be permanently attached to the body. The holder can be further provided with pairs of biasing triangles 44 which bias the tethers outwardly from the body when the cartridge is inserted into the holder during assembly. When the cartridge is activated, the tethers fold and position the over-travel cap to prevent the plunger and needle from being pulled out of the cartridge during retraction.

In use, with reference to FIGS. 3–7, an activatable cartridge-needle unit in accordance with this invention operates in conjunction with a disposable holder during and after administration of an injection site as follows. The syringe assembly is received by the health care worker and the plunger rod is detached from the body of the holder. The cartridge-needle unit is activated, i.e., the proximal end of the needle is caused to pierce the septum and the cartridge is moved forward in the hub, preferably by application of an axial and distal force to a tamper-evident cap. The flip top is then rotated out of the way to expose the post, e.g., a screw threaded post, of the plunger. The plunger rod is screwed onto the post. The needle is then inserted into the injection site, and the medication is delivered to the patient by the health care worker applying an axially and distally directed force to the plunger rod through the thumb pad. Thereafter, the syringe is removed from the injection site. Continued application of an axially and distally directed force on the plunger rod causes the cartridge to slide forward in the hub, breaking the washer-dart. This forces the dart through the septum and embeds the needle into the plunger. The plunger rod is then retracted, permanently capturing the needle, dart and plunger completely within the cartridge. The plunger and needle can be prevented from being pulled out of the cartridge by the auxiliary "over-travel" cap which can be snapped in place as the cartridge is activated.

The invention has been described in detail with particular reference to certain preferred embodiments thereof, but it will be understood that variations and modifications can be effected within the spirit and scope of the invention. For example, it is contemplated that an automatic needle withdrawal system can be implemented with this invention.

What is claimed is:

1. A cartridge-needle unit comprising:
   a cartridge comprising:
   a hollow body,
   a septum at the distal end of said body,
   means for retaining the septum, and
   a plunger, axially and reciprocally slidable through the interior of said body;
   a needle capable of being retracted within said cartridge;
   a hub comprising:

a sleeve adapted to be snapped on the distal end of said cartridge, means for retaining said needle within the hub during an injection; and means for releasing the needle from the hub after the injection comprising an element attached to said needle, said element having a diameter substantially greater than said needle and wherein said element and said needle are capable of passing through said septum as an assembly.

2. A cartridge-needle unit comprising:
a cartridge comprising:
  a hollow body,
  a septum at the distal end of said body,
  means for retaining the septum, and
  a plunger, axially and reciprocally slidable through the interior of said body;
a needle capable of being retracted within said cartridge;
a hub comprising:
  a sleeve adapted to be snapped on the distal end of said cartridge,
  means for retaining said needle within the hub during an injection; and
  means for releasing the needle from the hub after the injection comprising an element attached to said needle, capable of passing through said septum,
wherein said means for releasing the needle from the hub comprises:
  a washer, and
  a dart attached to said needle, wherein said dart is capable of passing through said septum.

3. The cartridge-needle unit of claim 2 wherein said dart is frangibly connected to said washer.

4. The cartridge-needle unit of claim 2 wherein said hub comprises a fluid well.

5. The cartridge-needle unit of claim 2 wherein said means for retaining the septum comprises an aluminum cap.

6. The cartridge-needle unit of claim 2 wherein said plunger comprises a stud.

7. The cartridge-needle unit of claim 2 wherein said hub comprises a post capable of forcing said dart through said septum.

8. The cartridge-needle unit of claim 2 wherein said dart is fabricated of a brightly colored plastic.

9. The cartridge-needle unit of claim 2 further comprising means for tilting the needle comprising a noncompliant member.

10. A syringe assembly comprising the cartridge needle unit of claim 2 and a holder therefor.

11. The syringe assembly of claim 10 wherein said holder is a disposable holder.

12. The syringe assembly of claim 10 wherein said holder comprises a cap sized to prevent the plunger and needle from being pulled out of the cartridge.

13. A syringe assembly comprising
a cartridge-needle unit comprising:
a cartridge comprising:
  a hollow body,
  a septum at the distal end of said body,
  means for retaining the septum, and
  a plunger, axially and reciprocally slidable through the interior of said body;
a needle capable of being retracted within said cartridge;
a hub comprising:
  a sleeve adapted to be snapped on the distal end of said cartridge,
  means for retaining said needle within the hub during an injection; and
  means for releasing the needle from the hub after the injection comprising an element attached to said needle capable of passing through said septum;
and a holder for said cartridge-needle unit;
wherein said holder comprises a cap and a connecting member between said cap and said holder.

14. The syringe assembly of claim 13 wherein said connecting member comprises a foldable tether.

15. The syringe assembly of claim 13 wherein said connecting member comprises means for predisposing the connecting member to fold in an outward direction.

16. The syringe assembly of claim 15 wherein said means for predisposing the connecting member to fold comprises a biasing triangle.

17. The cartridge-needle unit of claim 1 wherein said hub comprises a fluid well.

18. The cartridge-needle unit of claim 1 wherein said means for retaining the septum comprises an aluminum cap.

19. The cartridge-needle unit of claim 1 wherein said plunger comprises a stud.

20. The cartridge-needle unit of claim 1 further comprising means for tilting the needle comprising a noncompliant member.

21. A syringe assembly comprising the cartridge-needle unit of claim 1 and a holder therefor.

22. The syringe assembly of claim 21 wherein said holder is a disposable holder.

23. The syringe assembly of claim 21 wherein said holder comprises a cap sized to prevent the plunger and needle from being pulled out of the cartridge.

24. The syringe assembly of claim 21 wherein said holder comprises a cap and a connecting member between said cap and said holder.

25. The syringe assembly of claim 24 wherein said connecting member comprises a foldable tether.

26. The syringe assembly of claim 24 wherein said connecting member comprises means for predisposing the connecting member to fold in an outward direction.

27. The syringe assembly of claim 26 wherein said means for predisposing the connecting member to fold comprises a biasing triangle.

* * * * *